United States Patent
Courtney et al.

(10) Patent No.: US 10,429,304 B2
(45) Date of Patent: Oct. 1, 2019

(54) APPARATUS AND METHODS FOR IMAGING AND MODIFICATION OF BIOLOGICAL SAMPLES

(75) Inventors: Patrick Courtney, Beaconsfield (GB); Alistair Fitch, Beaconsfield (GB)

(73) Assignee: PerkinElmer Singapore PTE Ltd., Singapore (SG)

( * ) Notice: Subject to any disclaimer, the term of this patent is extended or adjusted under 35 U.S.C. 154(b) by 1097 days.

(21) Appl. No.: 12/162,444

(22) PCT Filed: Feb. 28, 2007

(86) PCT No.: PCT/GB2007/000698
§ 371 (c)(1),
(2), (4) Date: Nov. 12, 2008

(87) PCT Pub. No.: WO2007/099312
PCT Pub. Date: Sep. 7, 2007

(65) Prior Publication Data
US 2009/0298114 A1    Dec. 3, 2009

(30) Foreign Application Priority Data

Feb. 28, 2006 (GB) .................................. 0603923.4

(51) Int. Cl.
*C12Q 1/02* (2006.01)
*G01N 21/64* (2006.01)

(52) U.S. Cl.
CPC ..... *G01N 21/6458* (2013.01); *G01N 21/6408* (2013.01)

(58) Field of Classification Search
CPC ................................ A61L 2/08; G01N 33/487
USPC .................................................... 435/40.5, 6
See application file for complete search history.

(56) References Cited

U.S. PATENT DOCUMENTS

| | | | |
|---|---|---|---|
| 4,624,915 A | 11/1986 | Schindler | |
| 4,629,687 A | 12/1986 | Schindler et al. | |
| 5,998,129 A | 12/1999 | Schütze | |
| 6,514,722 B2 * | 2/2003 | Palsson et al. | 435/40.5 |

FOREIGN PATENT DOCUMENTS

| | | |
|---|---|---|
| EP | 0101572 | 2/1984 |
| WO | WO-2004/036892 A2 | 4/2004 |
| WO | WO-2004/036898 A2 | 4/2004 |

OTHER PUBLICATIONS

Castano et al. "A green fluorescent protein-expressing murine tumour but not its wild-type counterpart is cured by photodynamic therapy", British Journal of Cancer, Jan. 17, 2006, 94:391-397.*
Vindelev, "A Review of Techniques and Results Obtained in One . . . ", Cytometry, vol. 11, No. 7, 1990, pp. 753-770.
Merchant, "Strategies for Automated Fetal Cell Screening", Human Reproduction Update, vol. 8, No. 6, 2002, pp. 509-521.
Kensi, "Principle of Image Processing and Its Effect", First Edition, 2006, pp. 83-96.
Bulina et al., "A genetically encoded photosensitizer," Nature Biotechnology, 24(1): 95-99 (2006).
Dinur et al., "Administration of Pyrene-Sphingomyelin By Receptor-Mediated Endocytosis: Intracellular Degradation, Flow Cytometric Sorting of Normal and Niemann-Pick Cells, and Selective Photosensitization of the Latter," J. of Basic Clin. Physiol. and Pharmacol., 2(3): A19 (1991). Abstract.
Herweijer et al. "High-Speed Photodamage Cell Selection Using Bromodeoxyuridine/Hoechst 33342 Photosensitized Cell Killing," Cytometry, 9(2): 143-149 (1988).

* cited by examiner

*Primary Examiner* — Bin Shen
(74) *Attorney, Agent, or Firm* — Barnes & Thornburg LLP; G. Peter Nichols

(57) ABSTRACT

This invention relates to enrichment of a biological sample comprising a plurality of cells to assist further analysis thereof. It provides a technique comprising the steps of: (a) providing a sample comprising a plurality of cells which include a photosensitive compound that can be induced by light irradiation to inactivate or kill at least part of the respective cell; (b) acquiring an image of at least a portion of the sample; (c) identifying cells of interest in the sample image; (d) selecting cells other than the cells identified in step (c); and (e) irradiating only those cells selected in step (d) with a light beam so as induce the photosensitive compound therein to inactivate or kill at least part of those cells, and thereby enrich the sample with respect to the cells of interest for further analysis.

15 Claims, No Drawings

APPARATUS AND METHODS FOR IMAGING AND MODIFICATION OF BIOLOGICAL SAMPLES

RELATED APPLICATIONS

This application is a U.S. national stage application under 35 U.S.C. § 371(b) of International Application No. PCT/GB2007/000698, filed Feb. 28, 2007, which in turn claims the right of foreign priority under 35 U.S.C. 35 U.S.C. § 119(a) to Great Britain Patent Application No. 0603923.4, filed Feb. 28, 2006.

FIELD OF THE INVENTION

The present invention relates to modification of biological samples which comprise a plurality of cells. More particularly, it concerns enrichment of a sample with respect to cells of interest to assist further analysis thereof.

BACKGROUND TO THE INVENTION

During the study of biological samples, it is common to have samples that contain cells of particular interest within a mixture of cells. It may be useful to enrich the sample with respect to the cells of interest in the population for further processing and analysis.

This capability is of interest within the research area to provide an understanding of mechanisms of a cellular process, where the technique has applications for example in the study of cell differentiation, cell lineage and fate, of system development, in the area of regulation, in the response to any external stimulus, to provide new knowledge and understanding. This capability is also of interest for the diagnosis of a disease or disorder (detecting presence of a condition, evaluating the extent of a condition) by comparing the results with normals; and for evaluating the effectiveness of a treatment by looking at changes over time.

Typically, a particular cell type exists within a heterogeneous population of multiple cell types. Examples include differentiated cells within a tissue sample and stem cells [So 2004]; cancer cells and blood vessels within a tissue sample; neurons growing in a substrate of supporting cells; fetal cells in maternal blood; white blood cells of various types (natural killer cells, etc) in blood samples; metastatic cancer cells in tissues samples, etc. In addition a particular cell type may itself consist of a heterogeneous population with respect to some particular characteristic. For example, the cells may consist of subgroups of cells at different positions in the cell cycle, including being quiescent (non-dividing). In addition, the cells may be responding to the environment in different ways or be activated in different ways, and thus expressing different proteins or molecules of interest or entire processes or pathways.

One current approach to sort cells is to use a flow cytometer or a Fluorescence Activated Cell Sorter (FACS) machine. The practice is to label the cells with one or more fluorescent labels, to disperse the cells in a suitable carrier medium, and to pass that carrier medium containing the cells through the FACS machine, in which the carrier is formed into droplets by passing through a nozzle. The resulting droplet is exposed to a beam of excitation light, causing the fluorescent label in an individual cell to fluoresce and emit light which is detected in the form of a signal, which is used to form the basis of a classification decision to accept or reject the cell, and divert it into a receptacle for further processing. Multiple labels can be used to determine various states of the cell and thus make more complex classification decisions. Such an approach is able to sort cells at modest rates, with good discriminating ability when the fluorescent label has the necessary sensitivity and selectivity.

However this approach suffers from a number of drawbacks. Sample preparation and rough handling may perturb the sample and limits it to a single passage. This will be a problem if the cells exist in a supporting matrix and/or the interaction between cells is to be maintained so that only non-adherent cells are used. In addition, since the FACS process involves some delay, this means that some fine-grained temporal and kinetic information is lost making some studies very difficult eg synchronization of cell cycle. In addition, the data collected from each cell is of a fairly coarse nature, making it difficult to distinguish between distinct spatial organizations of the label, due e.g. to translocation processes.

In an alternative approach, the sample may be analysed manually under a microscope with a micro-dissecting stage. Markers (stains) may be added to allow different cell types, components and structures to be visualized, distinguished and manipulated. This is slow, laborious and error-prone, and it is difficult to prevent cross-contamination between sample components or the use of live objects. It is not feasible if the cell type is rare.

In a further technique, a laser may be used for microdissection and to cut around the cells of interest [Wittke 2005; Schuetze 1997]. This helps to prevent contamination problems. Alternatively, optical tweezers may be used to displace small scale biological objects, but cannot effectively perform certain types of operation such as the cutting or removal of undesired attached material. Laser ablation can also be used to remove unwanted material.

In an another approach, the sample may be lysed and probed for particular molecules or combinations of molecules such as DNA, RNA or proteins using a microarray. This approach can be very sensitive and selective. However it can be quite slow, preventing fine temporal information from being accessed, and it is generally destructive of the cell under study, thus preventing the collection and further use of cells of a particular type.

SUMMARY AND DETAILED DESCRIPTION OF THE INVENTION

The present invention provides a method of modifying a biological sample, comprising the steps of:
(a) providing a sample comprising a plurality of cells which include a photosensitive compound that can be induced by light irradiation to inactivate or kill at least part of the respective cell;
(b) acquiring an image of at least a portion of the sample;
(c) identifying cells of interest in the sample image;
(d) selecting cells other than the cells identified in step (c); and
(e) irradiating only those cells selected in step (d) with a light beam so as induce the photosensitive compound therein to inactivate or kill at least part of those cells, and thereby enrich the sample with respect to the cells of interest for further analysis.

The technique proposed herein involves locating and identifying the cells of interest from a population of live cells, preferably using one or more suitable markers, with suitable image acquisition instrumentation capable of targeting an irradiating light beam onto a specific cell or part of an unwanted cell. With the introduction of one or more suitable photosensitive compounds, the irradiating light beam acts to modify the photosensitive compound. Based on the appearance of a cell, a decision may be made to direct and activate the irradiating light beam, and thus result in the release of a species in such a way as to kill it.

Benefits of the present approach over the prior art are that it allows examination of greater numbers of samples than would be possible using a manually guided approach, and facilitates enrichment based on: rarer events (such as cancer metastasis); faster events or events with fine grained temporal information (such as phase synchrony); multiple events, coincident events or events separated in time or space; difficult to see events or fine spatial detail; events occurring over a longer time scale, and enrichment of greater quality (more true positives, less false positive, less contamination), and with less interference with the sample under study.

Preferred techniques have been developed by the present inventors for acquiring and analyzing images with marker probes and photo-sensitive compounds, which allows individual cells to be selectively irradiated and thus deactivated or killed.

Enrichment of a sample by eliminating only a proportion of the cells of interest may facilitate some long term studies (tracking changes over time), and/or modulation or manipulation of the interaction between cells types.

The use of a photosensitive compound enables enrichment in a well controlled manner, using a lower power light source (such as a low power laser) than is needed to destroy a cell using light alone.

The following steps are envisaged in one implementation:
1) Present sample consisting of mixed population of cells;
2) Probe with marker molecule;
3) Introduce photosensitive compound (optional);
4) Stimulate sample (optional);
5) View sample with viewing optics (various imaging modes);
6) Refine viewing parameters including focus (optional);
7) Acquire digital image set;
8) Process the image(s) to obtain an image measure;
9) Classify cell of interest based on coincidence of one or more image measures;
10) Direct an irradiating light beam to a particular location in the sample at a particular moment in time in order to carry out an action on the sample;
11) Repeat from step 3 (introduce) step 4 (stimulate) or step 5 (view); or
12) Exit and further processing of the sample.

The sample is typically a particular cell type within a heterogeneous population of multiple cell types. Examples include differentiating tissues with stem cells, progenitor, precursor and differentiated cells within a tissue sample.

Furthermore a particular cell type may itself consist of a heterogeneous population with respect to some particular characteristic. For example, the cells may consist of subgroups of cells at different positions in the cell cycle, including being quiescent (non-dividing).

Alternatively the population of cells may be a heterogeneous population of cells of different cell types, or with some genetic variation, mutation or phenotype, or with different degrees of transfection of an agent.

The cells may be responding to the environment in different ways or be activated in different ways, and thus expressing different proteins or molecules of interest or entire processes.

The sample may be part of a cell, an organelle and/or cell region in a cell. Alternatively the population of cells may be an assembly of cells in 2D or 3D; a tissue sample; a biological fluid such as blood; a biopsy sample; an organ; an embryo; a part of an animal or a plant; or an entire animal or a plant.

The marker molecule and photosensitive compounds may comprise one or more of the following: a fluorescence molecule; a luminescent molecule; an uncaging agent with an active part bound to a chromophore or fluorophore by a photo-cleavable link [Gurney 1999]; a ligand conjugated with a dye; a CALI reagent (a non-blocking antibody conjugated with a dye [Ilag 2000]); a photosensitizer such as KillerRed (marketed by Evrogen); a genetically encoded molecule such as GFP; a photo-activatable molecule such as genetically encoded PA-GFP or caged molecule [Sawin 1999]; a photo-switching molecule such as KFP; a timer protein [Terskikh 2000][Verkhusha 2004]; a cell cycle marker; a voltage or potential sensitive marker; a biosensor; a multi-functional marker probe (multi-functional marker probes indicate the presence of multiple species by changes in the excitation emission profile with the presence of metal ions [Komatsu 2005] or kinases/phospholipases [Schultz 2005]); an exogenous molecule that binds to a genetically encoded tag; a conjugated quantum dot; a conjugated metallic nanoparticle; a conjugated encapsulated fluorescent nanoparticle; or it may rely on the fluorescence of an intrinsic molecule. Exogenous (non-genetically encoded) markers may be cell permeable. Genetically and non-genetically encoded markers may be introduced or may have been previously introduced into cells by a number of known techniques.

Stimulation of the sample may include any external stimulus (biochemical, chemical, physical, thermal, optical, electrical, magnetic, electromagnetic, etc).

The imaging modes may include one or more of the following: fluorescence at one or more excitation wavebands; luminescence; widefield; confocal; phase contrast; DIC; structured illumination; fluorescence lifetime; polarization; or multi-photon processes.

The viewing parameters which may be modified may include the focus, plane of focus, field of view, excitation power level, wavelength and waveband, polarization, pulse regime, as well as detector parameters such as wavelength sensitivity, exposure timing and duration, location within a multi-sample holder, and the like.

The digital image set may comprise one or more of the following: bright-field images; fluorescence images; confocal images at particular focal planes; fluorescence lifetime images in a range; images at particular wavebands from the infrared to the ultraviolet; a time sequence; an image stack, or any combination of the above.

Suitable image measures may include cell location, boundary, extent; cell morphology; cell division or position in the cell cycle; cell viability; image features such as intensity, relative intensity, change in intensity, texture measures; lifetime, relative lifetime, change in lifetime; spectral shift; movement, migration or motility; outgrowth; a cellular or sub-cellular event such as translocation from cytoplasm to nucleus, membrane to nucleus, organelle to nucleus, membrane to cytoplasm, organelle to cytoplasm, nucleus to cytoplasm, cytoplasm to membrane, nucleus to membrane, organelle to membrane, cytoplasm to organelle, membrane to organelle, nucleus to organelle, endocytosis, exocytosis, invasion by a particle or virus; vesicle movement; membrane ruffling; cell blebbing; growth cone extension; particular pH value or range of pH values, particular ion concentration or range of ion concentration; DNA content; DNA fragmentation; membrane potential; number and size of DNA loci; binding event; signaling; adhesion; or other measurement such as current, voltage, impedance, or transconductance.

A classification decision may be made based on one or more measures falling above or below or within limits, comparison with a model, or statistical distance from a set of examples; or some linear or non-linear mapping of the measures; or a classifier based on nearest neighbour; artificial neural network; support vector machine; pattern recognition; or genetic algorithm.

The action carried out may inactivate or kill at least part of a cell. This may be achieved by flash photolysis, uncaging or releasing (a luminescence substrate such as luciferin [Yang 1993] or coelenterazine; free radicals) a toxic substance, perforation of a cell wall, transfection, ablation or other modification of specific structures such as microtubules; or activation of a pathway such as apoptosis.

Further processing or analysis can include examination, harvesting, sorting, culture or treatment of the sample by dispensing of reagents.

The invention further provides apparatus for carrying out the techniques described herein, which comprises: a detector for acquiring an image of at least a portion of the sample; a light source for generating a light beam to irradiate a selected region of the sample; and a controller arranged to manipulate the light source to only irradiate at least part of each of a plurality of selected cells.

Instrumentation which may be configured to provide steps 5 (view) to 10 (action) is described in an earlier patent application [Courtney 2005].

The classification step may be based on data obtained from previous acquisitions; acquired from other imaging modalities (X-ray, CT, MRI, PET); from databases, or other external sources.

The location, region and time point for the irradiation to take place may be based on information about the sample and the desired experimental protocol.

The apparatus may be configured to study a single sample or a larger sample requiring motion of the viewing location between locations. Additionally multiple samples may be presented on a larger carrier, whereby the samples differ in some way (different cells, different reagents, different environment).

Further applications of the techniques disclosed herein may include:
  screening for activity of drug candidates by observing changes;
  screening for safety of drug candidates or therapeutic agents;
  detecting the presence of a disease or disorder (diagnosis);
  evaluating the extent of a disease or disorder (stratification);
  evaluating the effectiveness of a treatment; and
  discovery of biomarker to indicate any of the above.

REFERENCES

P. Courtney et al, 2005, A method of analysing a sample and apparatus therefor, UK patent publication no. 2418018, in the name of PerkinElmer Singapore PTE Ltd.

W. Wittke and C. May, 2005, EP1537401: Carrier device for a biological preparation which can be cut by means of laser micro-dissection, Leica Microsystems.

K. Schuetze and R. Schuetze, 1997, EP0879408 B1: Method and Device for the contactless laser-assisted microinjection, sorting and production of biological objects generated in a planer manner, PALM.

P-L So and E. H. Epstein, Adult stem cells: capturing youth from a bulge? Trends in Biotechnology, Volume 22, Issue 10, October 2004, pp. 493-496.

J. Yang and D. B. Thomason, 1993, An easily synthesized, photolyzable luciferase substrate for in vivo luciferase activity measurement, Biotechniques. November, 15(5), pp. 848-50.

L. L. Ilag, J. H. Ng and D. G. Jay, 2000 Chromophore-Assisted Laser Inactivation (CALI) to Validate Drug Targets and Pharmacogenomic Markers. Drug Development Research 49, pp. 65-73.

A. Terskikh, A. Fradkov, G. Ermakova, A. Zaraisky, P. Tan, A. V. Kajava, X. Zhao, S. Lukyanov, M. Matz, S. Kim, I. Weissman and P. Siebert, 2000, Fluorescent Timer: Protein That Changes Color with Time, Science, 290 (5496), 24 November, pp. 1585-1588.

V. V. Verkhusha, D. M. Chudakov, N. G. Gurskaya, S. Lukyanov and K. A. Lukyanov, 2004, Common pathway for the red chromophore formation in fluorescent proteins and chromoproteins, Chem Biol. 2004 June; 11(6) pp. 845-54.

C. Schultz, A. Schleifenbaum, J. Goedhart and T. W. Gadella, 2005, Multiparameter imaging for the analysis of intracellular signalling, Chembiochem, August, 6(8), pp. 1323-30.

H. Komatsu, T. Miki, D. Citterio, T. Kubota, Y. Shindo, Y. Kitamura, K. Oka and K. Suzuki, 2005, Single Molecular Multi-analyte ($Ca^{2+}$, $Mg^{2+}$) Fluorescent Probe and Applications to Bioimaging, Am. Chem. Soc., 127 (31), pp. 10798-10799.

K. E. Sawin, J. A. Theriot and T. J. Mitchison, Photoactivation of Fluorescence as a Probe for Cytoskeletal Dynamics in Mitosis and Cell Motility. 1999, In Fluorescent and Luminescent Probes for Biological Activity: A Practical Guide to Technology for Quantitative Real-Time Analysis, Edited By W. Mason, Academic Press.

A. M. Gurney, Photolabile Caged Compounds. 1999, In Fluorescent and Luminescent Probes for Biological Activity: A Practical Guide to Technology for Quantitative Real-Time Analysis, Edited By W. Mason, Academic Press.

The invention claimed is:

1. A method of modifying a biological sample comprising a mixed population of cells by enriching the sample with respect to cells of interest, comprising the steps of:
  (a) providing a sample comprising a plurality of cells which include a photosensitive compound that can be induced by light irradiation to inactivate or kill at least part of the respective cell;
  (b) acquiring a time sequence of images of the plurality of cells;
  (c) identifying cells of interest in the sample images from said plurality of cells by analysis of the sequence of images acquired in step (b) by an image processing arrangement, the identification of cells of interest being based on detection of changes in the images indicating a predetermined event involving those cells occurring during the time sequence of images, wherein the cells are identified as of interest by reference to images or data relating to the sample and acquired using a different imaging modality to that employed in step (b);
  (d) selecting cells from said plurality of cells other than the cells identified in step (c); and
  (e) irradiating only those cells selected in step (d) by selectively directing a light beam to the selected cells to induce the photosensitive compound therein to inactivate or kill at least part of those cells, and to enrich the sample with respect to the cells of interest for further analysis.

2. A method of claim 1 wherein the sample comprises cells of different cell types, and in step (c) cells of a particular type are identified.

3. A method of claim 1 wherein the plurality of cells consists of cells of the same type, and in step (c) a subgroup of the plurality of cells which have a common characteristic is identified.

4. A method of claim 1 wherein the photosensitive compound is one of the following: a chromophore-assisted laser inactivation (CALI) reagent; an uncaging agent; a photosensitizer.

5. A method of claim 1 including a step of introducing the photosensitive compound into each of the plurality of cells.

6. A method of claim 1 wherein the photosensitive compound is genetically encoded in each of the plurality of cells.

7. A method of claim 1 wherein at least part of the selected cells is killed in step (e) by activation of apoptosis, or by the release of a toxic substance.

8. A method of claim 1 wherein the sample comprises cells which include a marker compound that is able to respond to light irradiation to assist analysis of the sample.

9. A method of claim 1 wherein the sample comprises one of: an assembly of cells in 2D or 3D; a tissue sample; a biological fluid; a biopsy sample; an organ; an embryo; a part of an animal or a plant; or an entire animal or a plant.

10. The method of claim 9 wherein the biological fluid is blood.

11. A method of claim 1 including a step of stimulating the sample prior to step (b).

12. A method of claim 1 wherein an image is acquired in step (b) using one of the following imaging techniques: fluorescence at one or more excitation wavebands; luminescence; widefield; confocal; phase contrast; differential interference contrast (DIC); structured illumination; fluorescence lifetime; polarization; or a multi-photon process.

13. A method of claim 1 wherein the sequence of acquired images comprises: bright-field images; fluorescence images; confocal images at particular focal planes; fluorescence lifetime images in a range; images at particular wavebands from the infrared to the ultraviolet; an image stack; or any combination thereof.

14. A method of claim 1 wherein said further analysis comprises one of: examination; harvesting; sorting; culture; or treatment of the sample by dispensing of reagents.

15. A method of modifying a biological sample comprising a mixed population of cells by enriching the sample with respect to cells of interest, comprising the steps of:
(a) providing a sample comprising a plurality of cells which include a photosensitive compound that can be induced by light irradiation to inactivate or kill at least part of the respective cell;
(b) acquiring a time sequence of images of the plurality of cells using one of the following imaging techniques: fluorescence at one or more excitation wavebands; luminescence; widefield; confocal; phase contrast; differential interference contrast (DIC); structured illumination; fluorescence lifetime; polarization; or a multi-photon process;
(c) classifying cells of interest in the sample images from said plurality of cells by analysis of the sequence of images acquired in step (b) by an image processing arrangement, the classification of cells of interest being based on detection of changes in the images, wherein the cells are classified as of interest by reference to images or data relating to the sample and acquired using a different imaging modality to that employed in step (b) and classified by at least one of: (i) comparing a measured parameter of a cell with a predetermined threshold; (ii) mapping a measured parameter; (iii) a classifier based on nearest neighbor; (iv) an artificial neural network; (v) a support vector machine; (vi) pattern recognition; or, (vi) a genetic algorithm;
(d) selecting cells from said plurality of cells other than the cells classified in step (c); and
(e) irradiating only those cells selected in step (d) by selectively directing a light beam to-the selected cells to induce the photosensitive compound therein to inactivate or kill at least part of those cells thereby enriching the sample with respect to the cells of interest for further analysis.

* * * * *